United States Patent [19]

Teng et al.

[11] Patent Number: 5,389,542
[45] Date of Patent: Feb. 14, 1995

[54] CONTROLLING VITRIFICATION OF PLANTS USING WATER ABSORBENT POLYMER

[75] Inventors: Whei-Lan Teng, Taipei Hsien; Yann-Jiun Liu, Chiayi Hsien; Tai-Sen Soong, Taipei, all of Taiwan, Prov. of China

[73] Assignee: Development Center for Biotechnology, Taiwan, Prov. of China

[21] Appl. No.: 970,679

[22] Filed: Nov. 4, 1992

[51] Int. Cl.⁶ .......................... C12N 5/00; C12N 5/02
[52] U.S. Cl. ................... 435/240.45; 435/240.1; 435/240.4; 435/240.54; 424/78.08
[58] Field of Search .......... 435/240.4, 240.54, 240.45, 435/240.1; 424/78.08; 514/964

[56] References Cited

U.S. PATENT DOCUMENTS 4,960,703 10/1990 Paques et al. ............... 435/240.4
4,980,434 12/1990 Farrar et al. ................. 526/240

FOREIGN PATENT DOCUMENTS 0101253 2/1984 European Pat. Off. .
0195550 9/1986 European Pat. Off. .
0247018 11/1987 European Pat. Off. .
8604919 8/1986 WIPO .

OTHER PUBLICATIONS

Williams, R. R. et al., "Effect of Temperature, gel concentration and cytokinins . . . shoot cultures," Plant Cell, Tissue and Organ Culture, 26, pp. 1–6, 1991.
Pasqualetto, P. L. et al., "Gelling Agent and Growth Requlator . . . in vitro," J. Amer. Soc. Hort. Sci., 111(6), pp. 976–980, 1986.
B. Leshem et al., Annals of Batony 61,255–260, 1988.
P. -L. Pasqualetto, "Plant Aging: Basic and Applied Approaches", 1990. ed. R. Rodriques et al. Plenum Press, New York, N.Y. pp. 133–137.
P. -L. Pasqualetto, Acta Horticulturae 227,352–357, 1988.

Primary Examiner—Douglas W. Robinson
Assistant Examiner—Kristen Larson
Attorney, Agent, or Firm—Fish & Richardson

[57] ABSTRACT

The present invention is directed to a method for reducing vitrification of a plant, especially lettuce, in a culture. Replacement of agar with water absorbent polymer successfully prevents vitrification without depressing organogenesis.

12 Claims, No Drawings

CONTROLLING VITRIFICATION OF PLANTS USING WATER ABSORBENT POLYMER

FIELD OF THE INVENTION

The present invention provides a method for controlling vitrification of plants.

BACKGROUND OF THE INVENTION

Vitrification of plants is a serious problem since it can affect shoot multiplication and culture vigor and can impede the successful transfer of micropropagated plants to in vivo conditions thereby limiting the application of the in vitro techniques as a means for mass propagation.

Affected plants exhibit tissue hyperhydricity and hypertrophy, deficiency of chlorophyll a and b, cell wall lignification lacking or limited to a layer opposed to the cell membrane, and leaves with large intercellular spaces in the spongy mesophyll, and with little differentiation between the mesophyll and palisade cells (Pasqualetto P. L., W. P. Wergin and R. H. Zimmerman, 1988, Changes in structure and elemental composition of vitrified leaves of 'Gala' apple in vitro, Acta Horticulturae 227: 352-367).

Some hypotheses have been proposed for the mechanism of vitrification, and there have been techniques developed to overcome vitrification by manipulating the culture conditions. However, most of the efforts have only limited success and a specific technique usually could not be applied to all plants.

For example, substituting Bacto-agar for Gelrite as a gelling agent could prevent vitrification in 'Gala' apple (Pasqualetto P. L., Zimmerman R. H. & Fordham I., 1986, The influence of gelling agent and growth regulator concentrations on vitrification of apple cultivars in vitro, J. Amer. Soc. Hort. Sci. 111: 976-980). For some other plants, however, vitrification could not be prevented by using agar as a gelling agent although it could be decreased to some extent by increasing the concentration of agar. Another example is that removal of cytokinin from the culture medium could reverse the vitrification in melon (Leshem B., Wreker E. & Shalev P. D., 1988, The effect of cytokinins on vitrification in melon and carnation. Ann Bot. 62: 271-276) and apple (Gaspar T., Kever C., Devergh P., Maene L., Pasques M. & Boxus P., 1987, Vitrification: morphological, physiological and ecological aspects, In: Bonga J. M., Durzan D. J., Eds, Cell and Tissue Culture in Forestry, Vol I pp.152-166 Martinus Nijhoff Publ, Dordrecht, Holland) while in cactus it showed no effect. In multiplication cultures of *Castanea sativa*, normal shoots and vitreous shoots were obtained when using Heller's or MS macronutrient, respectively (Pasqualetto P. L., 1990, Vitrification in plant tissue culture, In: Rodrigues R et al., Eds, Plant aging: Basic and Applied Approaches, pp.133-137, Plenum Press, New York). However, in globe artichoke, changes in the formulation of the major elements did not influence the result of vitrification. Besides, decreased vitrification is usually accompanied by a lower number of adventitious bud regenerations. Therefore, there are still needs for progress in controlling vitrification of plant.

Lettuce is an important vegetable and its in vitro culture is relatively easy. It has been used as a model plant for developing the artificial seeds of adventitious shoots. However, vitrification has proved to be a serious problem after a series of subcultures.

To solve the vitrification problem associated with lettuce cultures, we have tried to manipulate many factors which have been reported effective in limiting vitrification. These factors include culture temperature and concentrations of $Ca^{2+}$, $NH_4^+$, cytokinin, sucrose and polyethyleneglycol. We have also tried two commercial antivitrifying agents (EM1 and EM2, Pronatec Co., France). None of them showed any effect in decreasing vitrification of regenerated shoots.

We surprisingly found that the replacement of agar in a solid culture with water absorbent polymer can minimize vitrification of lettuce without significantly reducing shoot regeneration.

DISCLOSURE OF THE INVENTION

It is the main object of the present invention to provide a method for controlling vitrification of a plant which is characterized by adding water absorbent polymer in the culture medium.

Although numerous gelling agents have been reported in restricting vitrification, the present invention of water absorbent polymer to solidify medium has never been reported. Water absorbent polymer is widely applied in the field as one of the plant transplanting/transporting media to prevent water loss and provide a root system with sufficient moisture. This study extends the application of water absorbent polymer to in vitro culture.

There are many water absorbent polymers suitable for the present invention. The preferred water absorbent polymers are those capable of absorbing water from about 50 to about 800 times its weight. The most preferred water absorbent polymers are those capable of absorbing water from about 100 to about 250 times its weight; for instance, acrylamide acrylate copolymer is capable of absorbing water up to about 200 times its weight.

The suitable amount of water absorbent polymer depends on the species of plant and the culturing conditions. The necessary amount of water absorbent polymer with a higher water absorbing capacity is lower. Generally, water absorbent polymer present in an amount from about 0.1 g to about 10 g per 50 ml medium is preferred. The higher the content of water absorbent polymer results in higher water absorption and better efficacy in controlling vitrification.

The method for controlling vitrification of the present invention is not limited to lettuce cultures. It can also be used to control vitrification of Lactuca sp. and other species of plants.

As shown by the EXAMPLE, the method of controlling vitrification of the present invention using water absorbent polymer can significantly restrict the vitrification of plant without significantly depressing organogenesis.

Although a water absorbent polymer may somewhat suppress the growth of regenerated shoots, it could be applied during shoot regeneration to achieve normal shoot regeneration because it is known that the occurrence of a stable vitrified or normal growth pattern is determined in the initial stages of the culture. Once normal shoots are regenerated, they can then be transferred to agar medium to accelerate the growth of shoots.

The replacement of agar in the culture medium with a water absorbent polymer can also reduce the cost of medium.

The following example is offered to aid in understanding of the present invention and is not to be construed as limiting the scope thereof.

EXAMPLE

1. Plant material

Plant material for this study was long-term subcultured Green callus (with buds) of 'Great Lake 118' lettuce. Inoculum was prepared by osterizing green callus (with buds) with the culture medium for 60 seconds. The inoculum, composed of single cells and aggregates of a few cells, has a size sufficiently small to pass through 400μ (42-mesh) stainless steel sieves.

2. Medium

The medium used for experiments was SH medium (Schent P. V. & Hilderbrandt A. C., 1972, Medium and techniques for induction and growth of monocotyledonous and dicotyledonous plant cell culture. Can. J. Bot., 50: 199-204) supplemented with 1.5% glucose, 100 mg/l myoinositol and 0.5 μM NAA (naphthalene acetic acid) and BA (6-benzyladenine). The pH of the medium was adjusted to 5.8 before autoclaving.

3. Water absorbent polymer

The water absorbent polymer used in this study was SuperSorb provided by Aquatrols Co. U.S.A.. It is a acrylamide acrylate copolymer. There are two types of SuperSorb: SuperSorb C (coarse, particle size of 1-3 mm) and SuperSorb F (fine powder). SuperSorb is capable of absorbing water up to about 200 times its weight and releasing nearly 100% of that water on demand.

4. Method

In this study, 3.3 ml of inoculum was pipetted into vessels containing 50 ml of the culture medium and various amounts of SuperSorb. Agar was used as the gelling agent in the control experiment. All the experiments were repeated twice.

5. Results

When SuperSorb was first applied, the color of inoculum turned from green to dark brown within one week. It was suspected that this might result from a certain toxic pigment contained in the SuperSorb. After thoroughly washing the SuperSorb, the green color of the inoculum remained unchanged and shoot regeneration occurred.

TABLE 1

The effects of polymer SuperSorb (acrylamide/acrylate copolymer, Aquatrols Corp., U.S.A.) on vitrification of lettuce regeneration on solid medium.

| SuperSorb (g/50 ml) | Shoot Normal (no vessel) | Total | Normal shoot as a % of total |
|---|---|---|---|
| Coarse | | | |
| 0.25 | 30 | 188 | 16.0 |
| 0.50 | 21 | 88 | 23.9 |
| 1.00 | 9 | 9 | 100.0 |
| Fine | | | |
| 0.25 | 16 | 193 | 8.3 |
| 0.50 | 61 | 186 | 32.8 |
| 1.00 | 129 | 129 | 100.0 |
| Control | 55 | 209 | 26.3 |

Means were sperated by Dunken's New multiple range test, $p = 0.05$.

As shown from Table 1, 100% of normal shoots was achieved by adding 1 g of SuperSorb to 50 ml culture medium and depression of organogenesis did not occur when SuperSorb F(fine) was used.

Although SuperSorb F(fine) at 1 g/50 ml was able to achieve 100% normal shoot regeneration, shoot growth took a longer time compared with the control treatment. Thus, the regenerated shoots were transferred to an agar medium for further growth. Once transferred to the agar medium, the regenerated shoots resumed growth rapidly.

While the invention has been described with respect to a preferred exemplification, it is not intended to limit the scope of the invention thereby, but solely by the claims appended hereto.

We claim:

1. A method for reducing vitrification of a plant in a growth medium, which comprises the step of adding a water absorbent acrylamide/acrylate copolymer to the growth medium, said copolymer, which is capable of absorbing water from about 50 to about 800 times its weight, being added in an amount necessary to reduce the vitrification.

2. A method as claimed in claim 1, wherein the plant is a Lactuca sp.

3. A method as claimed in claim 2, wherein the plant is *Lactuca sativa*.

4. A method as claimed in claim 1, wherein the water absorbent polymer is added in an amount of from about 0.1 g to about 10 g to a 50 ml culture medium.

5. A method as claimed in claim 4, wherein the water absorbent polymer is added in an amount of about 1 g to 50 ml culture medium.

6. A method as claimed in claim 4, wherein the plant is Lactuca sp.

7. A method as claimed in claim 6, wherein the plant is *Lactuca sativa*.

8. A method as claimed in claim 5, wherein the plant is Lactuca sp.

9. A method as claimed in claim 8, wherein the plant is *Lactuca sativa*.

10. A method of claim 1, wherein said polymer being capable of absorbing water from about 100 to about 250 times its weight.

11. A method as claimed in claim 8, wherein the plant is Lactuca sp.

12. A method as claimed in claim 9, wherein the plant is *Lactuca sativa*.

* * * * *

UNITED STATES PATENT AND TRADEMARK OFFICE
CERTIFICATE OF CORRECTION

PATENT NO.    : 5,389,542
DATED         : February 14, 1995
INVENTOR(S)   : Whei-Lan Teng, Yann-Jiun Liu and Tai-Sen Soong It is certified that error appears in the above-identified patent and that said Letters Patent is hereby corrected as shown below:

Column 1, lines 37-38, "in vitro", substitute --*in-vitro*--.

Column 3, line 10, after "material" insert a --:--.

Column 3, line 33, substitute --acrylamide acrylate-- for "acrylamide/acrylate".

Column 3, line 64, substitute --no.-- for "no".

Column 4, line 7, substitute --no.-- for "no".

Column 4, line 15, after "0.05." insert --Total refers to the sum of both normal and abnormal regenerated shoots.--

Column 4, line 26, substitute --an agar-- for "the agar".

Column 4, claim 4, line 46, substitute --in-- for "to a".

Column 4, claim 11, line 61, substitute --10-- for "8".

Column 4, claim 12, line 63, substitute --11-- for "9"

Signed and Sealed this

Twenty-fifth Day of June, 1996

Attest:

BRUCE LEHMAN

*Attesting Officer*        Commissioner of Patents and Trademarks